United States Patent [19]

Brody

[11] Patent Number: 4,467,479

[45] Date of Patent: Aug. 28, 1984

[54] METHOD OF SURGICALLY REPAIRING AN INJURED HUMAN JOINT AND A PROSTHETIC DEVICE THEREFOR

[76] Inventor: Garry S. Brody, 219 Tilden, Los Angeles, Calif. 90049

[21] Appl. No.: 346,277

[22] Filed: Feb. 5, 1982

[51] Int. Cl.³ .............................. A61F 1/04; A61F 5/04
[52] U.S. Cl. ..................................... 3/1.91; 128/92 C; 3/1
[58] Field of Search ................ 128/92 C; 3/1.9, 1.91, 3/1.912, 1.911

[56] References Cited

U.S. PATENT DOCUMENTS 4,052,753 10/1977 Dedo ........................... 128/92 C X Primary Examiner—Richard J. Apley
Assistant Examiner—D. J. Isabella
Attorney, Agent, or Firm—Edward J. DaRin

[57] ABSTRACT

A method of surgically repairing an injured human joint such as a finger joint by means of a prosthetic device. The prosthetic device comprises a U-shaped sack partially filled with a pressure sensitive material. The prosthetic device is implanted between two bones comprising the injured joint in a manner to control the growth of the scar capsule at the joint to prevent the joint from becoming stiff. The pressure sensitive material in the sack moves between the two bones in response to any slackness of the scar to fill out the slackness and thereby prevent shortening of the scar that would restrict motion.

5 Claims, 9 Drawing Figures

U.S. Patent  Aug. 28, 1984  4,467,479
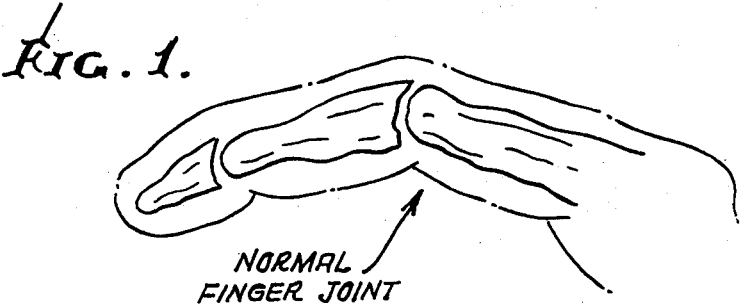
Fig. 1. NORMAL FINGER JOINT
Fig. 9. PD
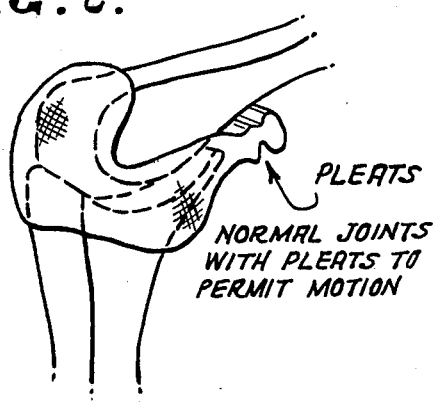
Fig. 2. PLEATS — NORMAL JOINTS WITH PLEATS TO PERMIT MOTION
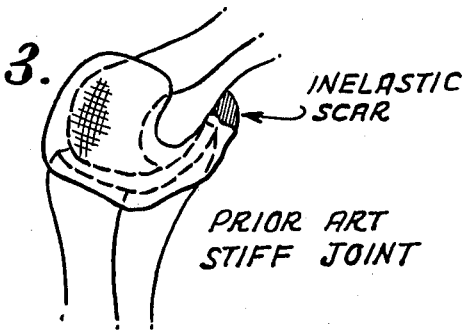
Fig. 3. INELASTIC SCAR — PRIOR ART STIFF JOINT
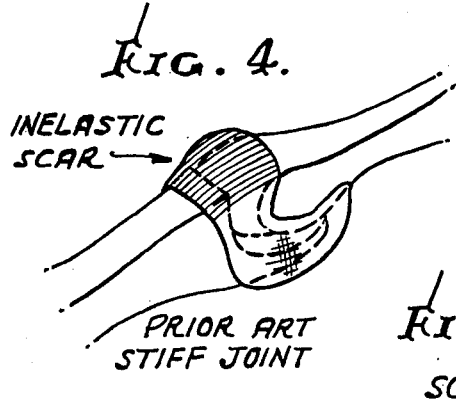
Fig. 4. INELASTIC SCAR — PRIOR ART STIFF JOINT
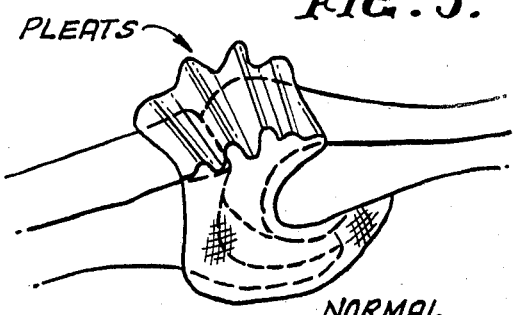
Fig. 5. PLEATS — NORMAL JOINT
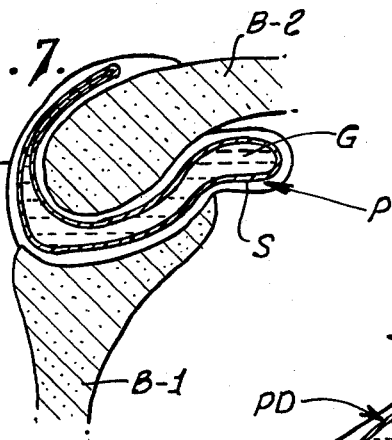
Fig. 7. B-2, SC, G, PD, S, B-1
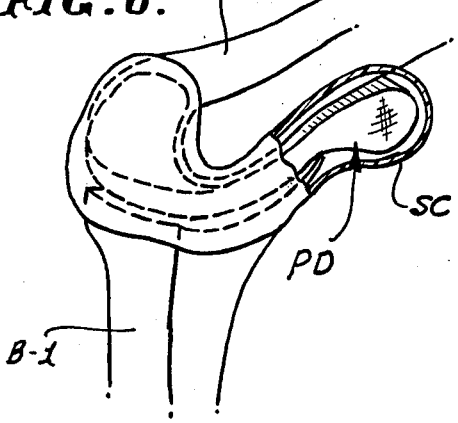
Fig. 6. B-2, SC, PD, B-1
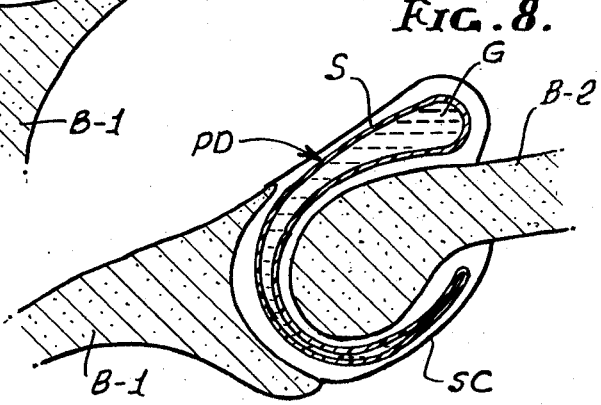
Fig. 8. S, G, B-2, PD, B-1, SC

METHOD OF SURGICALLY REPAIRING AN INJURED HUMAN JOINT AND A PROSTHETIC DEVICE THEREFOR

FIELD OF INVENTION

This invention relates to an improved prosthetic device for repairing injured human joints such as finger joints, or the like, and a method of surgically repairing an injured joint by implanting the joint with the improved prosthetic device to closely simulate a natural joint.

BACKGROUND OF THE INVENTION

The repair of damaged human finger joints and the like has been accomplished heretofore surgically through the use of several different types of joints or hinges. These prior art joints include hinged joints, flexible rubber, ball sockets, and various others. The problems of repairing or replacing the finger joints does not appear to reside in the design of the joint hinge, but the fact that a tight scar capsule forms around the repaired joint and limits the motion thereof.

SUMMARY OF THE INVENTION

The present invention provides an improved prosthetic device that can be readily implanted to repair a damaged human joint such as a finger joint, or the like, without the problems inherent in prior art devices or methods, namely, the shrinkage of the scar capsule around the repaired joint to the extent of restricting the normal movement of the repaired joint. The prosthetic device per se of the present invention comprises a flexible sack implantable between the adjacent surface of the bones at the damaged joint once the damaged scar tissue is reshaped. The flexible sack includes a pressure sensitive gel partially filling the sack to maintain the normal spacing between the bone surfaces and to maintain sufficient tension on the growth of new scar tissue to prevent the formation of an inelastic scar capsule to shrink around the joint so as to restrict the normal movement of the finger at the joint. The flexible sack may comprise a synthetic elastomer, such as a silicone elastomer, having a flexible gel-like material therein, such as a silicone gel. The gel has been selected so as to respond to any slackness in the scar to move between the bones to prevent shortening of the scar that restricts motion. Once the scar is mature, the scar tissue shrinkage problem disappears and the prosthetic device could be removed, if it is troublesome, or left intact, since its purpose has been served at that time. If the flexible sack is made from silicone, the silicone surfaces should stimulate the formation of a cartilage-like cover for the ends of the bone.

From a broad method standpoint of surgically repairing an injured human joint, such as a finger joint, the method comprises the steps of reshaping the injured tissue between the two bones forming the human joint in preparation to accept the prosthesis device and, after this preparatory step, placing a preselected prosthesis device, that is constructed and defined to form an interface between the two adjacent surfaces of the bone, between the two adjacent surfaces comprising the joint. The prothesis device is further characterized as maintaining the distance between the two bone surfaces to thereby control the growth of the new scar tissue around the joint to prevent the new scar tissue from shrinking around the joint in a manner so as to restrict the normal movement of the joint.

From a structural standpoint of the joint, prosthesis for a human finger comprises a flexible sack containing a pressure sensitive material partially filling the sack, the sack having a U-like configuration to be positioned between the two adjacent surfaces normally forming the space in the joint. The pressure sensitive material has a depth so that the normal spacing between the bones is maintained and to permit normal movement at the thus defined joint while controlling the growth of the scar tissue normally formed around the joint by maintaining the scar tissue in sufficient tension to prevent the shrinkage of the scar tissue around the sack in a manner to restrict motion of the finger joint. The sack may be constructed of a silicone elastomer having a silicone gel partially filling the silicone balloon. The sack, when constructed of a silicone material, provides lubrication to the joint and is biologically tolerable when it is encapsulated with the new scar tissue.

These and other features of the present invention may be more fully appreciated when considered in the light of the following specification and drawings, in which:

BRIEF DESCRIPTION OF THE DRAWINGS

FIG. 1 is a diagrammatic representation of a normal human finger showing the arrangement of the finger bones therein;

FIG. 2 is a diagrammatic representation of a normal finger joint illustrating the pleats of the normal capsule on the bottom side of the finger that permits normal motion of the joint;

FIG. 3 is a diagrammatic representation of the prior art stiff finger joint that has healed with an inelastic scar formed on the bottom side of the scar capsule to restrict the movement at the joint;

FIG. 4 is a diagrammatic representation of the prior art stiff finger joint that has healed with an inelastic scar on the top surfaces of the finger joint;

FIG. 5 illustrates a normal finger joint with the pleats on the top side of the finger that permit normal movement at the joint;

FIG. 6 illustrates a finger joint repaired with the prosthetic device embodying the present invention;

FIG. 7 is a cross-sectional illustration of a finger joint with the prosthetic device of the present invention implanted therein and illustrating the finger bones in an angular relationship;

FIG. 8 is a diagrammatic representation of a finger joint illustrating the relationship of the prosthetic device of the present invention when the finger has been moved so that the joint is extended; and FIG. 9 is a detached view of the prosthetic device prior to being implanted at the finger joint.

DETAILED DESCRIPTION

Now referring to the drawings, the prosthetic device PD of the present invention will be described in detail. Initially, reference will be made to FIGS. 1, 2, and 5, which illustrate a normal finger joint for a finger in order to obtain a better appreciation of the concept of the present invention. A human finger has a multiplicity of joints therein, as is evident from FIG. 1. In the normal finger joint the bones are completely separated and are held close to each other by a tough, fibrous, covering attached above and below the two ends of the bones. This covering is called the joint capsule. The joint capsule usually has a lining which pours out a lubricating fluid into the joint space so as to keep the ends of the bones that move against one another moist or lubricated. The surfaces of the ends of the bones are made of a cartilage which is not so hard as bone and therefore gives a little when they are pressed to form sort of a cushion at the joint. In FIG. 2 it will be noted that the normal finger joint, when flexed to an angle of approximately 90 degrees will cause the joint capsule to form pleats on the bottom side of the finger, but adjacent to the joint, which permits normal finger movement. Specifically, when the finger is moved so that the joint is extended, the pleats on the top side of the finger permit the capsule to be elongated without restricting the movement of the finger; see FIG. 5.

The problems of the uses of prior art prosthetic devices are that they permit a new scar capsule formed at the repaired joint to compress around the joint so as to render the joint stiff, and thereby incapable of normal movement. FIG. 3 shows the inelastic scar that results adjacent the bottom side of the finger joint, while the inelastic scar illustrated in FIG. 4 is on the topside of the finger joint. The formation of the inelastic scar occurs after injury whether or not a prior art prosthetic device is implanted. It should be appreciated that with the joint capsule shrinking around the joint and not providing the pleated surfaces, such as in FIGS. 2 and 5, the joint will not be capable of normal movement, due to the tightness with which the scar capsule has enclosed the joint when the prior art prosthetic devices and methods are utilized.

The concept of the present invention is to provide a prosthetic device that is readily implantable between the two bones of a finger joint, or the like, and that does not permit the scar capsule to shrink around the joints so as to restrict the joint or render it stiff after it has healed. In particular, the joint implant of the present invention is constructed and defined so that the surgically repaired finger joint closely simulates the motion and anatomy of a natural joint, i.e., unrestricted movement at the joint.

FIG. 9 illustrates the detached flexible balloon-like prosthesis device PD which embodies the present invention. The prosthesis device PD is illustrated as a sack having a pressure sensitive material partially filling the sack. The sack PD has a U-like configuration so that it may be implanted between the two bones of a damaged finger joint while partially encircling the end of one of the bones, as is evident from FIGS. 7 and 8 in particular. In the presently preferred embodiment of the invention, the prosthetic device comprises a sack or balloon S constructed of a silicone elastomer having a silicone gel G partially filling the sack S. The silicone material has been selected for this purpose to provide lubrication to the joint and a biologically tolerable spacer when it is implanted therein and encapsulated by a new scar capsule SC. In FIGS. 6, 7 and 8, the two bones that form the finger joint that is being repaired are identified as bone B-1 and bone B-2. As is usual in surgery, the damaged scar tissue in the space between the bones B-1 and B-2 is shaped by conventional surgical techniques in preparation for implanting the prosthetic device PD therein. The prosthetic device PD includes a pressure sensitive material therein which, in its presently preferred embodiment, may be a silicone gel G. The volume of gel G stored within the sack S is proportioned to maintain the normal spacing between the bones B-1 and B-2; see FIG. 1. The gel G only partially fills the volume of the sack S to cause it to respond to any slackness of the scar by moving between the bones to prevent the shortening of the scar and thereby prevent the mature scar from restricting motion.

The generally U-shaped configuration provided for the prosthetic device PD permits it to be partially wrapped around the bone B-2 and to be positioned within the space normally forming the space in the joint. Once the device PD is implanted in this fashion and the gel G is of sufficient depth to maintain a normal spacing between the opposite edges of the bones B-1 and B-2 it will maintain sufficient spacing between the ends of the bones to prevent the scar capsule SC from shrinking or compressing around the joint to produce a stiff joint of the type in FIGS. 3 and 4 by the aforementioned responsive action of the gel G. Stated differently, the implanted device PD controls the growth of the new scar tissue to simulate a normal functional capsule. If, during the surgery, it is necessary to shape the edge of the bones B-1 and B-2, they are so shaped by conventional surgical techniques by the surgeon prior to placing the prosthetic device between the two bones surfaces. After the device PD is implanted, the repair of the injured joint is completed by the usual surgical techniques. With the formation of the new scar capsule around the finger joint, the purpose of the prosthetic device PD will have been accomplished. The device PD will permit the repaired joint to function much in the manner of a normal finger joint with the gel G within the sack S permitting normal movement at the joint, including cushioning the ends of the finger bones.

It should now be appreciated that the present invention has advanced the state of the art by providing a prosthetic device that controls the growth of a new scar capsule without rendering the repaired joint stiff.

I claim:

1. A method of surgically repairing an injured human joint with a prosthesis including the steps of providing a prosthesis comprising a balloon-like device having a U-like configuration and constructed of a synthetic, elastomeric material having a biologically tolerable material having a preselected pressure sensitive material partially filling the balloon, reshaping the injured tissues surrounding the joint, providing a space between the two opposing surfaces of the bones of said joint, positioning within said space said prosthesis and completely filling the joint space therebetween to maintain the distance between the two bone surfaces thereby permitting normal movement at said joint to thereby control the growth of new scar tissue around the joint during healing to prevent the new scar tissue from shrinking around the joint in a manner so as to restrict the normal movement of the joint after it healed.

2. A method of surgically repairing an injured human joint as defined in claim 1, wherein the balloon-like prosthesis is mountable between said two bone surfaces with at least a portion of the device partially surrounding at least one of said bone surfaces.

3. A method of surgically repairing an injured human joint, as defined in claim 1, including the step of shaping the surfaces of the bones prior to placing the prosthesis between said two bone surfaces.

4. A method of surgically repairing an injured human joint, as defined in claim 1, wherein said elastomeric balloon comprises a shaped silicone elastomer partially filled with a pressure sensitive silicone gel material to permit normal movement at the joint during healing including cushioning the ends of the joint bones.

5. A method of surgically repairing an injured human joint as defined in claim 1 or 2 wherein the human joint is a finger joint.

* * * * *